United States Patent
Cerman

(10) Patent No.: US 10,625,024 B2
(45) Date of Patent: Apr. 21, 2020

(54) MAGNIFYING DEVICE FOR A MEDICAMENT INJECTION DEVICE

(71) Applicant: SANOFI-AVENTIS DEUTSCHLAND GMBH, Frankfurt am Main (DE)

(72) Inventor: Zdenek Cerman, Idstein (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 159 days.

(21) Appl. No.: 15/549,064

(22) PCT Filed: Feb. 10, 2016

(86) PCT No.: PCT/EP2016/052766
§ 371 (c)(1),
(2) Date: Aug. 4, 2017

(87) PCT Pub. No.: WO2016/128426
PCT Pub. Date: Aug. 18, 2016

(65) Prior Publication Data
US 2018/0021520 A1    Jan. 25, 2018

(30) Foreign Application Priority Data

Feb. 10, 2015    (EP) .................................... 15154489

(51) Int. Cl.
| | |
|---|---|
| *A61M 5/315* | (2006.01) |
| *A61M 5/31* | (2006.01) |
| *A61M 5/24* | (2006.01) |
| *A61M 5/32* | (2006.01) |

(52) U.S. Cl.
CPC .......... *A61M 5/31568* (2013.01); *A61M 5/31* (2013.01); *A61M 5/3155* (2013.01);
(Continued)

(58) Field of Classification Search
CPC .......... A61M 5/31573; A61M 5/31556; A61M 2205/583; A61M 2205/585; A61M 2005/3126
See application file for complete search history.

(56) References Cited

U.S. PATENT DOCUMENTS

| | | | |
|---|---|---|---|
| 2,586,581 A | 2/1952 | Tschischeck | |
| 6,936,032 B1 * | 8/2005 | Bush, Jr. ........... | A61M 5/31551 |
| | | | 604/187 |

(Continued)

FOREIGN PATENT DOCUMENTS

| | | |
|---|---|---|
| CA | 2445511 | 11/2002 |
| CN | 1976735 | 6/2007 |

(Continued)

OTHER PUBLICATIONS

International Search Report and Written Opinion in International Application No. PCT/EP2016/052766, dated Apr. 11, 2016, 13 pages.

(Continued)

*Primary Examiner* — Nathan R Price
*Assistant Examiner* — Anh Bui
(74) *Attorney, Agent, or Firm* — Fish & Richardson P.C.

(57) ABSTRACT

The present disclosure relates to a magnifying device attachable to an injection device. The magnifying device includes a frame having a distal end and having a proximal end opposite to the distal end and further has a receptacle extending from the distal end towards the proximal end. The receptacle is accessible from the distal end to receive a proximal end section of the injection device therein. A magnifying lens is fixed to the proximal end of the frame and extending at least partially across the proximal end of the frame.

21 Claims, 3 Drawing Sheets

(52) U.S. Cl.
CPC .... *A61M 5/31556* (2013.01); *A61M 5/31573* (2013.01); *A61M 5/2466* (2013.01); *A61M 5/3286* (2013.01); *A61M 2005/3126* (2013.01); *A61M 2205/0216* (2013.01); *A61M 2205/502* (2013.01); *A61M 2205/583* (2013.01); *A61M 2205/585* (2013.01); *A61M 2205/586* (2013.01)

(56) References Cited

U.S. PATENT DOCUMENTS

| | | | |
|---|---|---|---|
| 2005/0143675 | A1 | 6/2005 | Neel et al. |
| 2006/0206057 | A1 | 9/2006 | Deruntz et al. |

FOREIGN PATENT DOCUMENTS

| | | | | |
|---|---|---|---|---|
| CN | 202896035 | | 4/2013 | |
| CN | 104271184 | | 1/2015 | |
| JP | S55-127188 | | 10/1980 | |
| JP | 2002-517289 | | 6/2002 | |
| JP | 2005-138568 | | 6/2005 | |
| JP | 2005-138567 | * | 7/2005 | ............ B43K 23/08 |
| JP | 2005/193637 | | 7/2005 | |
| JP | 2005-193637 | | 7/2005 | |
| JP | 2005193637 A | * | 7/2005 | ............ B43K 23/00 |
| JP | 2012-507314 | | 3/2012 | |
| WO | WO 01/10484 | | 2/2001 | |
| WO | WO 2013/037754 | | 3/2013 | |
| WO | WO 2014/128156 | | 8/2014 | |
| WO | WO 2014/139921 | | 9/2014 | |

OTHER PUBLICATIONS

International Preliminary Report on Patentability in International Application No. PCT/EP2016/052766, dated Aug. 15, 2017, 9 pages.

* cited by examiner

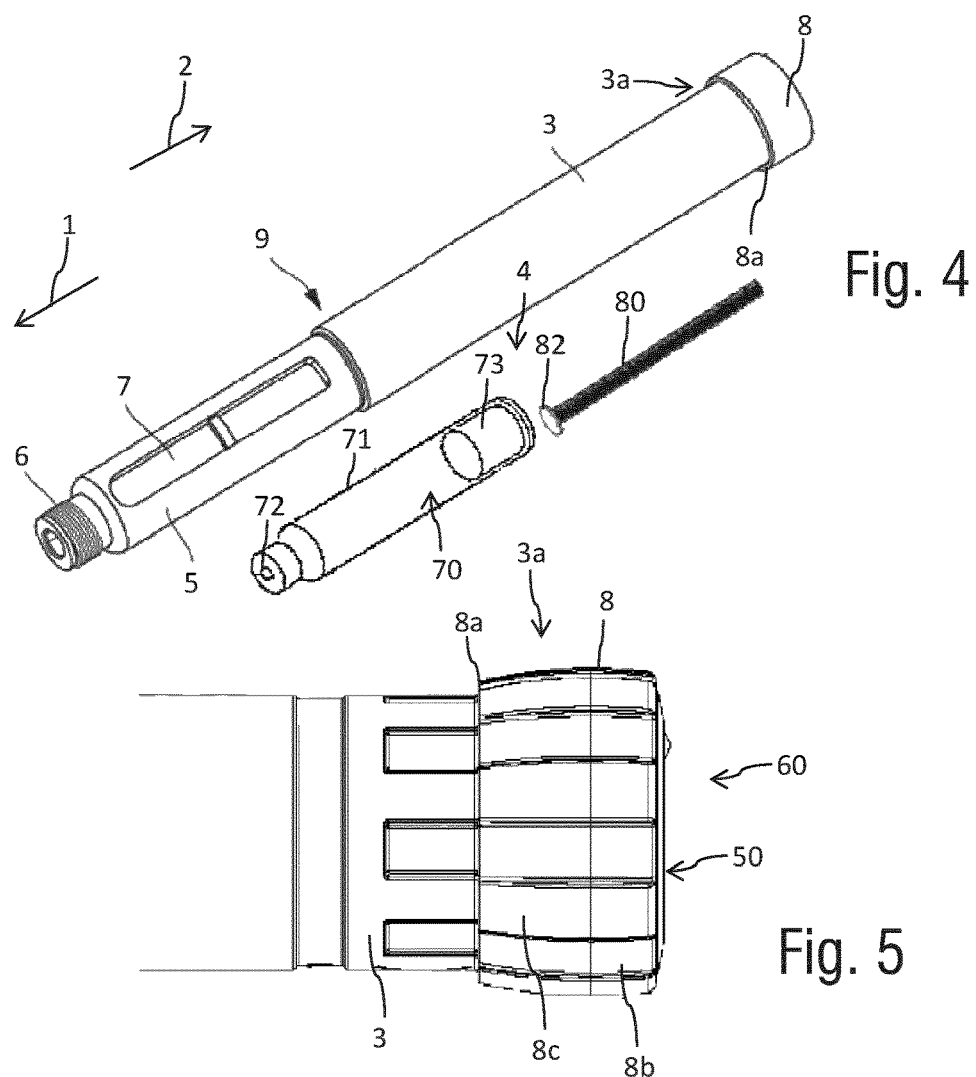
Fig. 4
Fig. 5
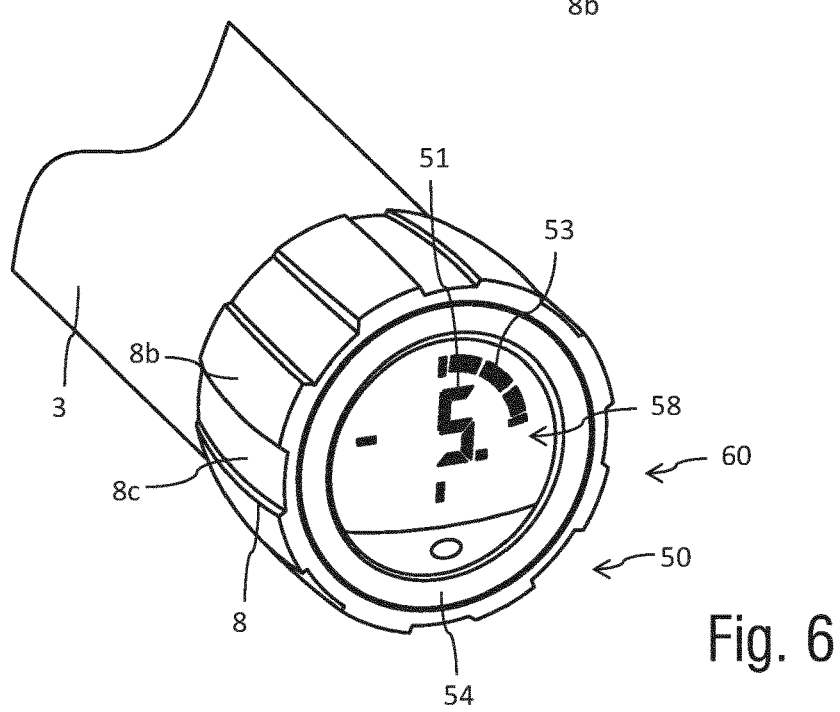
Fig. 6

MAGNIFYING DEVICE FOR A MEDICAMENT INJECTION DEVICE

CROSS-REFERENCE TO RELATED APPLICATIONS

This application is a U.S. national stage application under 35 USC § 371 of International Application No. PCT/EP2016/052766, filed on Feb. 10, 2016, which claims priority to European Patent Application No. 15154489.7, filed on Feb. 10, 2015, the entire contents of which are incorporated herein by reference.

TECHNICAL FIELD

The present disclosure relates to a magnifying device attachable to an injection device, such like a pen-injector. The magnifying device is particularly configured to magnify the visual appearance of information displayed on or at the injection device. The magnifying device is particularly adapted to magnify the visual appearance of a dose size indication and/or of a last dose display to inform a user about the size and the time when a last or previous dose has been delivered by the injection device. The disclosure further relates to an injection device, such like a pen-type injector comprising such a magnifying device.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be entirely discarded when the medicament in the cartridge has been completely dispensed or used-up.

Injection devices of pen-injector type typically provide the functionality of setting a dose of variable size and subsequently dispensing or injecting the dose actually set. Such devices typically have a dose size indicator, such like a number sleeve with a sequence of numbers or symbols printed on its outer circumference and being rotatably or helically arranged inside a housing. The housing typically has an aperture or a window through which a particular number of the scale of the number sleeve is visible, thereby representing the size of a dose actually set. Apart from such mechanically implemented dose size indicators there exist also electronically implemented dose size indicators making typically comprising an electronic display.

In general, there exist different configurations, a large variety and different types of dose size indicators. Document US 2011/0270214 A1 for instance discloses a pen-injector with a dosage selector at its proximal end and having a display arranged in an electronic module housing which is arranged in the dosage selector housing. There is further described a memory module for a drug delivery device that provides the user with information in respect of the last delivered dose, hence the amount and time since the last delivery.

The size of a display arranged in a dosage selector is rather limited due to the limited diameter of the dosage selector and the rather filigree and compact overall design of the pen-injector. Especially for elderly patients that may suffer from poor vision it may be rather difficult to correctly read the information provided on such a display. In addition, the rather compact design and dimensions of a dosage selector may impose difficulties also for the correct handling of the dosage selector. Due to its limited size and comparatively small diameter the circumferential gripping area of such dosage selectors is rather limited.

SUMMARY

The present disclosure provides an improved overall handling of an injection device and to provide a simple and effective means to simplify dose setting as well as reading of dose related information provided on a display or dose indicator of the injection device. The improvements should be easy to realize. The operation and functionality of the improvements should be rather intuitive and easily understandable. Moreover, the improvements regarding handling of the injection device and reading of dose information should be retrofittable to existing injection devices featuring a dosage selector equipped with a display.

In a first aspect a magnifying device attachable to an injection device is featured. The magnifying device comprises a frame having a distal end and having a proximal end. The distal end and the proximal end are located at opposite ends of the frame. Hence, the proximal end is located opposite to the distal end of the frame. The frame further has a receptacle or a cup-shaped recess extending from the distal end towards the proximal end. Typically, the receptacle is of elongated shape and extends in a longitudinal or axial direction from the distal end towards the proximal end. The receptacle is further accessible from the distal end to receive a proximal end section of the injection device, which proximal end section is typically provided with a display arrangement.

The magnifying device further comprises a magnifying lens fixed to the proximal end of the frame and extending at least partially across the proximal end of the frame. The magnifying lens may form a part of the proximal end of the frame and may be integrated into the frame. Also, the magnifying lens may be fixedly attached to the proximal end of the frame so as to cover the display arrangement of the injection device located underneath. Typically, the magnifying lens delimits or confines the receptacle in proximal direction. The receptacle is typically closed in proximal direction. The magnifying lens may thus form a bottom or end cap of the receptacle or of the respective frame.

By inserting the proximal end section of the injection device into the receptacle its display arrangement located at a proximal end face is magnified by the magnifying lens. In addition, the frame is attachable to the outer circumference of the proximal end section of the injection device, which proximal end section is rotatable and/or axially displaceable by a user for setting and/or for dispensing of a dose of a liquid medicament. By arranging and attaching the frame to the proximal end section of the injection device, the frame and hence the magnifying device also represents and provides a gripping aid and handling aid for a user of the device.

By arranging the proximal end section of the injection device inside the receptacle formed by the magnifying device's frame, the proximal end section of the injection device is operable and actuatable via the magnifying device. Depending on the overall geometry and dimensions of the frame, in particular depending on a radial expansion or thickness of the frame, the overall diameter of the proximal end section of the injection device can be enlarged by way of attachment of the frame.

The magnifying device therefore fulfills a double function. In a first aspect it provides a visual magnification of a display provided on the proximal end face of the injection device. In a further aspect it serves as a gripping aid and overall handling aid for dialing or actuating an actuation member at the proximal end of the injection device, which actuation member is typically implemented as a dose selector and/or as a dose button or dispensing button.

According to another embodiment the magnifying lens is arranged in a proximal end face of the frame. Typically, the proximal end of the frame comprises a through opening, which is completely covered by the magnifying lens. The magnifying lens may be integrated into the proximal end face of the frame. It may flush with a border of the frame's proximal through opening. Additionally or alternatively it may axially protrude from the proximal end face of the frame. Depending on the desired degree of magnification, the curvature of the magnifying lens may vary. Typically, the magnifying lens is arranged in a radial center of the frame's proximal end face. It may be centrally located in or at the proximal end face of the frame. In this configuration the magnifying device is particularly adapted to be attached to a circular symmetric dose selector at a proximal end section of the injection device.

The magnifying device is by no way limited to be assembled to injection devices or components thereof having a circular geometry. The magnifying device and the receptacle thereof may be universally adapted and configured to match with a large variety of differently shaped injection devices. For instance, the frame and the receptacle of the magnifying device may be also suitable to receive a proximal end section of injection devices featuring a triangular, quadratic, rectangular or oval shape.

The magnifying device is typically releasably attachable to the injection device. It may be provided as a separate device to positively or frictionally connect to the proximal end section of the injection device. In this way, the magnifying device provides retrofitting of existing injection devices with a combined visual magnifying means and a handling or gripping aid.

In a further embodiment the frame comprises a sidewall structure to enclose a dose selector located at the proximal end section of the injection device. The sidewall structure extends in a distal direction from the proximal end of the frame. Hence, the distal end of the sidewall structure forms an access opening for the magnifying device's receptacle. The proximal end of the sidewall structure is connected to the proximal end of the frame. It is typically connected to a proximal end face of the frame to which or in which the magnifying lens is arranged. The optical axis of the magnifying lens typically extends in longitudinal direction.

When attached to the injection device the optical axis of the magnifying lens may extend substantially parallel or may coincide with a longitudinal direction of the injection device. The sidewall structure may also extend parallel to the optical axis of the magnifying lens and may extend substantially parallel to the longitudinal axis of the injection device when attached thereto. Alternatively, it is conceivable that the sidewall structure extends at a predefined angle with regard to the longitudinal axis of the injection device. In particular, the sidewall structure may be conically-shaped or the thickness of the sidewall structure may be tapered towards the proximal end or towards the distal end of the frame.

In a further embodiment the sidewall structure is tapered towards the distal end of the frame. Hence, the sidewall structure and also the frame radially outwardly diverge towards the proximal end of the frame. This may have the benefit of providing a constantly increasing outer circumference and/or overall size of the outer surface of the frame or its sidewall structure towards the proximal end thereof. Hence, towards the proximal end, the magnifying device features a substantially enlarged circumference and radial diameter so as to facilitate and simplify gripping and overall handling of the dose selector. In addition, with a radially widened profile or diameter towards the proximal end also the diameter of the magnifying lens may increase to improve the quality and the legibility of the magnified information provided on the display of the injection device.

In another embodiment the sidewall structure comprises at least one radially inwardly extending latch or snap feature at the distal end to axially engage with a radially inwardly extending ledge at a distal end of the dose selector. Typically, the radially inwardly extending ledge of the sidewall structure axially and radially engages with the correspondingly-shaped ledge of the dose selector. Typically, at the radially inwardly extending ledge the dose selector terminates in distal direction. The ledge of the dose selector just forms a recess or stepped down portion on the outer circumference of the injection device. With the radially inwardly extending ledge the frame, hence its sidewall structure may be clipped onto the dose selector for at least providing axial engagement and axial fixing of the frame to the dose selector. At least the radially inwardly extending ledge of the sidewall structure exhibits a particular flexibility so as to snap over the distal ledge or distal edge of the dose selector.

According to a further embodiment the frame also comprises a radially inwardly extending rim portion at its proximal end. The rim portion comprises a distally-directed abutment face to axially abut with a proximal end face of the dose selector. Hence, the surface normal of the abutment face is directed in distal direction. The axial or longitudinal distance between the rim portion and the at least one radially inwardly extending ledge at the distal end of the sidewall structure typically matches and communicates with the axial elongation of the dose selector. In this way, a slack-free attachment of the frame to the dose selector can be provided.

Typically, the at least one ledge at the distal end of the sidewall structure radially and axially engages with the correspondingly-shaped ledge or edge at the distal end of the dose selector as the rim portion of the frame axially abuts with the proximal end face of the dose selector.

Typically, the ledge and the distal end of the sidewall structure provides a latch or snap feature audibly engaging with the correspondingly-shaped ledge or edge of the dose selector. In this way, an audible and/or haptic feedback is given to a user when the radially inwardly extending ledge of the frame engages with the correspondingly-shaped ledge or edge of the dose selector, thereby indicating to a user, that the magnifying device has been securely fitted to the dose selector and hence to the proximal end section of the injection device.

According to another embodiment the rim portion also comprises a proximally directed and radially inwardly extending abutment face in axial abutment with the magnifying lens. Hence, a distally-facing support section of the magnifying lens is in axial abutment with a proximally-facing abutment face of the rim portion. In this way, the magnifying lens is not only radially fixed to the frame but is also axially supported by the frame. In other words, via the mutual abutment of the magnifying lens and the frame in axial direction, the magnifying lens is also operable to transfer a distally directed thrust or pressure towards the frame and hence towards the frame's rim portion in axial abutment with the proximal end face of the dose selector.

Moreover, the rim portion of the frame may be axially sandwiched between the magnifying lens and the proximal end face of the dose selector. In this way, the magnifying lens is depressible in distal direction so as to transfer a respective pressure or thrust directly and unalteredly to the dose selector. The dose selector may thus act as a dispense or actuation button, by depressing of which a dispensing or injection process of the injection device may be at least triggered or controlled.

In another embodiment the sidewall structure comprises a cylindrically or conically-shaped sidewall. Here, the sidewall structure comprises a rather closed geometry. The frame with its distal end face and the cylindrically or conically-shaped sidewall may represent a cup-shaped and rather closed receptacle, which is only open in distal direction but which is closed and confined in radial and circumferential direction by the sidewall structure. In proximal direction, hence at its proximal end the frame may be closed and covered by the magnifying lens, optionally in combination with the radially inwardly extending rim portion.

The frame may be integrally formed and may consist of only one piece. The frame may be configured as an injection molded component. The frame may comprise an injection molded plastic material. It may comprise thermoplastic materials as well as thermoplastic elastomeric materials and mixtures and combinations thereof. It is particularly conceivable, that the magnifying lens is over-molded or insert molded by a respective injection moldable material. In this way, a separate step of assembly of frame and magnifying lens becomes superfluous. Manufacturing the magnifying device by means of insert molding or over-molding is therefore rather cost efficient and suitable for a mass manufacturing of such magnifying devices.

According to another embodiment the sidewall structure comprises at least two bendable legs extending in distal direction and being separated along the circumference of the frame's proximal end. The bendable legs may be arranged and separated at regular circumferential distances. The legs may be arranged equidistantly along the circumference of the frame's proximal end. When having two bendable legs, the legs are typically provided geometrically opposite on the outer circumference of the frame's proximal end. The legs typically extend in longitudinal direction towards the distal end of the frame. In this embodiment, the free end of the bendable legs form the distal end of the frame. Also, the legs may comprise a radially inwardly extending ledge to engage with a correspondingly-shaped ledge or edge at a distal end of the dose selector.

It is particularly intended to provide a plurality of bendable legs, e.g. three, four, five, six, eight or even more legs around the outer circumference of the frame's proximal end. When having four legs, the legs are typically separated by 90° according to a circular outer circumference of the frame. When having six legs, the circumferential offset between neighboring legs equals to about 60°, and so on. Depending on their overall geometric structure and shape, the legs are typically bendable radially outwardly with their free end against an inherent restoring force by way of which the bendable legs, in particular their free ends are typically biased or pre-tensed radially inwardly.

By means of at least two or even more bendable legs a rather simple and straight forward attachment of the frame to the proximal end section of the injection device can be provided. In comparison to a closed cylindrically or conically-shaped sidewall, the sidewall structure with at least two bendable legs may be made of a rather inelastic material providing a rather robust design of the frame and the magnifying device. The circumferential or tangential dimensions of the bendable legs may differ. The circumferential or tangential size of a leg may be as small as only a few degrees according to the outer circumference of the substantially circular-shaped dose selector. The tangential size may be also as large as almost 180° as seen in circumferential direction. In such an extreme configuration the two bendable legs may be just separated by a longitudinal slit in a cylindrically or conically-shaped sidewall of the sidewall structure.

Alternatively, it is also conceivable that the cylindrically or conically-shaped sidewall just comprises a single slit extending in longitudinal or axial direction so as to increase the radial flexibility of the sidewall's distal end.

According to another embodiment the sidewall structure comprises axially extending gripping ribs on at least one of its radially outwardly-facing portion or on at least a radially inwardly-facing portion. Typically, axially extending and radially outwardly protruding gripping ribs are separated by respective grooves located therebetween. In this way, the outer circumference of the sidewall structure comprises a rather rippled or corrugated surface inherently providing a good and beneficial gripping by at least two fingers of a user.

By means of radially inwardly extending gripping ribs a mechanical connection of the frame to the dose selector can be improved. The griping ribs are typically located on the inwardly-facing portion of the sidewall structure, hence on an inside-facing portion of the cylindrical or conical sidewall or on the inside-facing portion of bendable legs of the sidewall structure. They may even support a positive engagement or force-fitting engagement of the magnifying device and the dose selector.

According to another embodiment the sidewall structure is engageable with the dose selector in a torque-proof manner. Such a torque-proof engagement can be obtained by means of radially inwardly extending gripping ribs of the frame's sidewall structure engaging with correspondingly-shaped radially outwardly extending gripping ribs provided on the dose selector. Moreover, it is conceivable, that the outer circumference of the dose selector and the inner circumference of the sidewall structure of the frame comprise mutually corresponding interlock features, such like at least one pair of a radial groove mating and engaging with a correspondingly-shaped radial protrusion.

According to a further embodiment, the frame, its sidewall structure or at least a portion thereof comprises an elastomeric material. It is conceivable, that the entire frame is made of only one elastomeric material. Alternatively, the frame may comprise a rather inelastic material and may comprise at least in sections an elastomeric material on at least one of the radially inwardly-facing surface of the sidewall structure or the radially outwardly-facing surface of the sidewall structure. By means of an elastomeric material, a friction coefficient between the frame and the dose selector can be increased so as to provide a torque-proof and slack-free attachment and mutual engagement of the magnifying device to the dose selector.

Having an elastomeric material on the outer circumference of the sidewall structure provides a slip-free and comfortable handling of the dose selector. Moreover, it is even conceivable that the proximal end of the frame is provided with or consists of an elastomeric material. The elastomeric material may also provide a kind of a shock absorber for the dose selector and the display located therein. It is also conceivable that the proximal end of the frame comprises an axial recess in which the magnifying lens is located. When the magnifying lens does not axially protrude from such a proximal recess, the lens is effectively protected against breakage or other mechanical damage by the circumference of the frame's proximal end.

Apart from that and the specific embodiments described above the magnifying device with its frame and the magnifying lens may generally serve as a mechanical shock absorber when attached to the proximal end section of the injection device.

In another aspect an injection device for administering, hence for dispensing and injecting of a dose of a liquid medicament, is featured. The injection device comprises an elongated housing to receive a cartridge at least partially filled with the medicament to be delivered. The cartridge typically comprises a tubular-shaped barrel. The interior of the barrel is sealed in proximal direction by means of a piston slidably disposed inside the barrel. A proximal end of the barrel is typically sealed by a pierceable seal, which is to be penetrated by a double-tipped injection needle. By displacing the piston inside the barrel, typically in distal direction, the internal fluid pressure inside the barrel can be raised, thereby expelling a predefined amount of the medicament via the injection needle.

The injection device may be of disposable type or of reusable type. With a disposable device, the cartridge is readily mounted inside the housing. After consumption or after use of the medicament located inside the cartridge the entire device is intended to be discarded. With a reusable device the cartridge is replaceable by a new one when emptied. With reusable devices, the housing comprises two housing sections, typically a proximal housing section to receive a drive mechanism and a distal housing section to accommodate the cartridge.

The injection device further comprises a drive mechanism having a piston rod to operably engage with the piston of the cartridge. The drive mechanism comprises numerous mechanically interacting components by way of which a dose of variable size can be set and subsequently dispensed. Typically, during dose setting the piston rod is immobile and positionally fixed relative to the housing. It is exclusively displaceable in distal direction during a subsequent dose dispensing procedure thereby displacing the piston of the cartridge accordingly for expelling a predefined amount of the medicament.

The injection device further comprises a dose selector at a proximal end section of the housing. The dose selector is typically rotatably supported on or inside the housing to set a dose of variable size. The dose selector may not only be rotatably supported relative to the housing but may be also axially displaceable relative to the housing. It is conceivable, that the dose selector is somehow threadedly engaged with the housing so that a rotation of the dose selector for the purpose of setting of a dose is accompanied by an axial displacement of the dose selector relative to the housing, typically in proximal direction.

The dose selector may be also operable for dispensing of a dose, at least to trigger a dose dispensing action of the injection device. Hence, the dose selector may be depressible in distal direction so as to induce, to trigger or to control a dose dispensing process. The injection device further comprises a display arrangement in a proximal end face of the dose selector to visualize at least a dose information.

The injection device further comprises a magnifying device as described above, which magnifying device is attached to the dose selector. By means of the magnifying device attached to the dose selector the dose information visualized on the display arrangement is visually magnified. Moreover, the frame at least partially enclosing the outer circumference of the dose selector serves as a gripping aid for operating the dose selector, in particular for dialing of the dose selector for the purpose of setting of a dose of the medicament.

According to a further embodiment the dose selector is rotatable relative to the housing for at least setting of a dose. The magnifying device is further in torque-proof engagement with the dose selector. By means of a torque-proof engagement of dose selector and magnifying device, in particular of dose selector and frame of the magnifying device a slack-free and slip-free attachment of magnifying device and dose selector is provided. Thanks to a torque-proof and slack-free engagement of the magnifying device and the dose selector a rather precise and improved handling of the dose selector, in particular dialing of a dose can be provided even to users that are physically and/or visually impaired.

According to another embodiment the display arrangement is an electronic display arrangement to visualize the size of a last dose previously injected and to visualize a time interval since the last dose has been dispensed or injected. In addition or alternatively the electronic display arrangement is operable to visualize a point in time of a last dose delivery, further to visualize the time or date at which the device has been used for the first time, an expiry date of the medicament and/or a prescription schedule or a respective diary or other injection related information. The display arrangement may be also implemented as a mechanical display configured to visualize a size of a dose actually set and/or to visualize the size of a dose of an injection last delivered. Hence, the display arrangement may be configured to visualize the amount of a medicament and a time, either a point of time or a time interval since the last delivery of a dose took place.

The time interval since the last dose could be represented by symbols representing circle-segments. By arranging such symbols tangentially next to each other, each symbol may represent a discrete time interval, such like an hour. Then, the arrangement of several symbols may be easily countable like the display of an analog watch. In addition or alternative to such symbols the electronic display may further show some numbers, representing the size of the last dose.

In the present context, the distal direction points in the direction of the dispensing and of the device, where a needle assembly is typically provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, the dose selector or some other actuating member is located at the proximal end of the injection device, which is directly operable by a user to be rotated for setting of a dose and which may be further operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38[Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two p sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab=)2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE FIGURES

In the following some embodiments of the magnifying device and its attachment to an injection device are described in detail by making reference to the drawings, in which:

FIG. 5 is indicative of an enlarged side view of the injection device's proximal end, FIG. 6 is a perspective view of the proximal end of the injection device.

DETAILED DESCRIPTION

Figure 1:
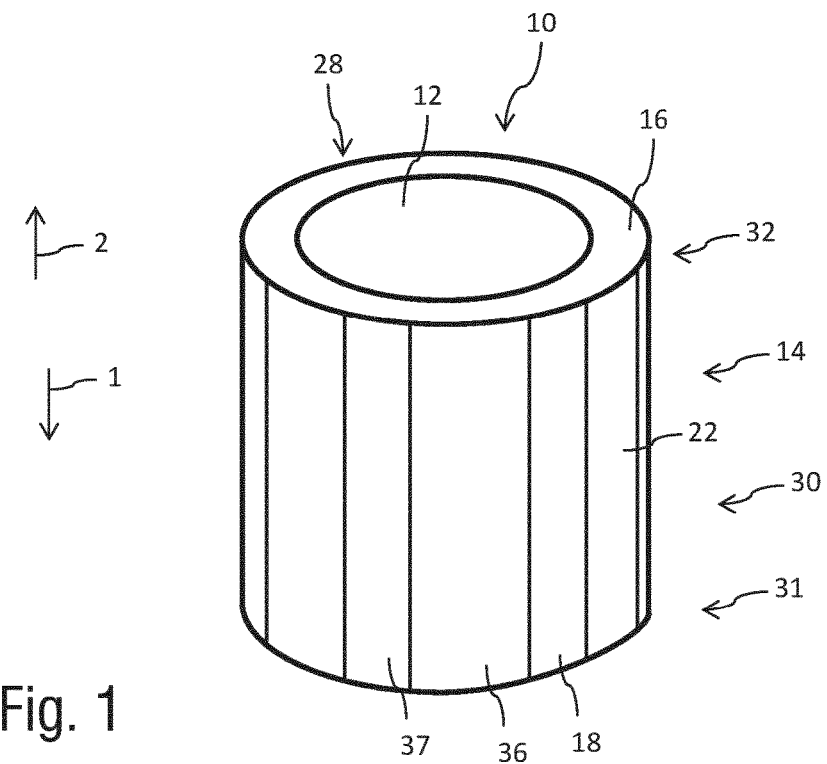
FIG. 1 schematically shows the magnifying device in a perspective illustration.

In FIG. 4 an injection device 9 of pen-injector type is schematically illustrated. The injection device 9 comprises a housing formed by a proximally-located body 3 and a distally-located cartridge holder 5. The body 3 forming a proximal end 3a of the injection device 9 is configured to house a drive mechanism 4, which drive mechanism 4 at least comprises an elongated piston rod 80 having a pressure piece 82 at its distal end to engage with a piston 73 of a cartridge 70 located inside the cartridge holder 5. The cartridge 70 comprises a tubular-shaped barrel 71 and it is filled with a liquid medicament. The distal end of the cartridge 70 is sealed by a pierceable seal 72, typically by means of a pierceable septum. The piston 73 forms a proximal seal of the interior volume of the cartridge 70.

By means of the piston rod 80 advancing in distal direction 1 during a dose injection or dose dispensing procedure the piston 73 is displaceable in distal direction 1 accordingly, thereby expelling a predefined amount of the medicament through an injection needle (not illustrated) penetrating the distal seal 72 of the cartridge 70. The injection needle is typically supported by a needle hub that is releasably mounted to a distal socket 6 of the cartridge holder 5. As shown in FIG. 4, the socket 6 comprises an outer thread to engage with a correspondingly-shaped inner thread of the needle hub. The cartridge holder 5 is further provided with an inspection window 7 by way of which the filling level as well as the constitution of the medicament contained in the cartridge 70 can be visually inspected.

When the injection device 9 is configured as a reusable device the proximal end of the cartridge holder 5 is releasably connectable to a distal end of the body 3. Consequently, the cartridge holder 5 is disconnectable from the body 3 in order to obtain access to the cartridge 7 located therein. When the content of the cartridge 70 is used up, the cartridge is replaceable by a new one. Upon cartridge replacement also the drive mechanism 4 is resettable and after reconnecting of cartridge holder 5 and body 3 the content of another cartridge 70 is dispensable.

At its proximal end 3a the injection device 9 comprises a dose selector 8. As shown in more detail in FIGS. 5 and 6, the dose selector 8 is of substantially tubular shape and exhibits a substantially circular-shaped cross-section. The dose selector 8 is rotatable relative to the body 3 with respect to a longitudinal axis thereof for setting of a dose of variable size. By turning or dialing the dose selector 8 clockwise or counterclockwise a dose may either be increased or decreased. It is further conceivable, that the dose selector 8 is not only rotatably supported on or in the body 3 but that the dose selector 8 is also axially displaceable relative to the body 3.

In comparison to an initial configuration as illustrated in FIGS. 4 and 5 the dose selector 8 may extend proximally from the body 3 as a dose of significant size is set or dialed. The size of the axial displacement of the dose selector 8 relative to the body 3 may be directly correlated and may represent the size of the dose actually set. Moreover, the dose selector 8 may further serve as a dose button to trigger or to induce a dose dispensing or dose injection process. Depressing of the axially extended dose selector 8 in distal direction 1 may induce a distally directed displacement of the piston rod 80. The specific implementation of a mechanical and/or electronic interaction between the dose selector 8 a dose display and the piston rod 80 may be realized in many different ways as they are commonly known in the prior art. As an example, the drive mechanism 4 of the injection device 9 may be implemented in a way as illustrated in document US 2011/0270214 A1, the entirety of which is herein incorporated by reference.

Figure 7:
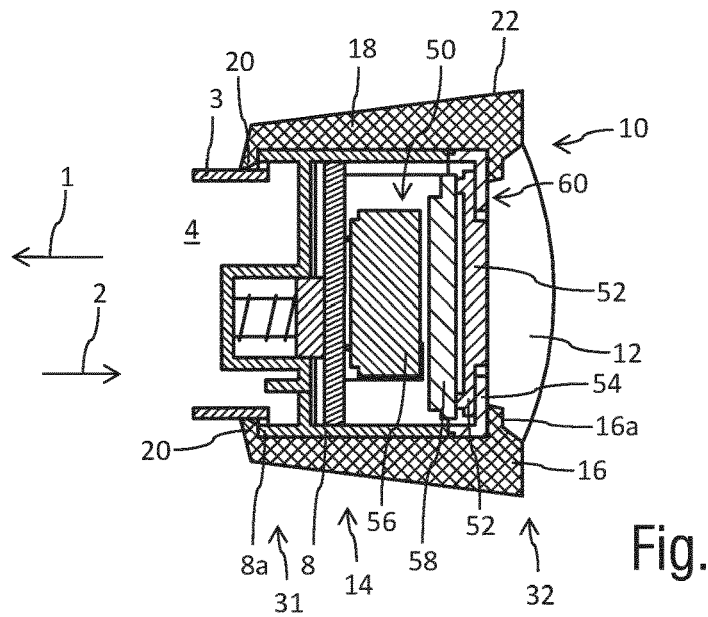
FIG. 7 is a longitudinal cross-section through the assembly of magnifying device and injection device.

As it is apparent from FIGS. 6 and 7 the injection device 9 comprises a display arrangement 50 at its proximal end face 60. As schematically shown in FIG. 6 the display arrangement 5 is for instance operable to visualize a size of a dose as well as a time interval since the particular dose has been dispensed. The display arrangement 50 presently implemented as an electronic display, typically of liquid crystal type, shows a number 51 representing the size of the last delivered dose. Moreover, the display arrangement is operable to visualize various symbols 53 arranged side-by-side in circumferential direction. In the present embodiment, each one of the symbols 53 represents a time interval of one hour since the last delivery of the dose took place.

The display arrangement 50 may be operable to permanently visualize and to permanently display the dose-related information. However, it is also conceivable, that the display arrangement 50 is switched on and switched off, e.g. by an axial sliding motion of the dose selector 8 or by activation of any other operating component of the injection device 9.

The display arrangement 50 as shown in cross-section in FIG. 7 comprises a dosing detector 56 by means of which the size and at least the time of a last delivered dose can be electronically detected and stored in a memory. The display arrangement 50 further comprises a display 58, typically in form of one or several liquid crystal cells. In addition, the display arrangement 50 comprises a transparent cover 52, which is fixed relative to the display 58 by means of a frame 54 mechanically connected to the dose selector. As shown in FIG. 7, the interior of the dose selector 8 is substantially hollow to receive the display arrangement 50.

In general, the display arrangement 50 may be implemented and configured in many different ways. As an example, the display arrangement 50 is implemented in a way as illustrated in document US 2011/0270214 A1, the entirety of which is herein incorporated by reference.

Figures 2, 3:
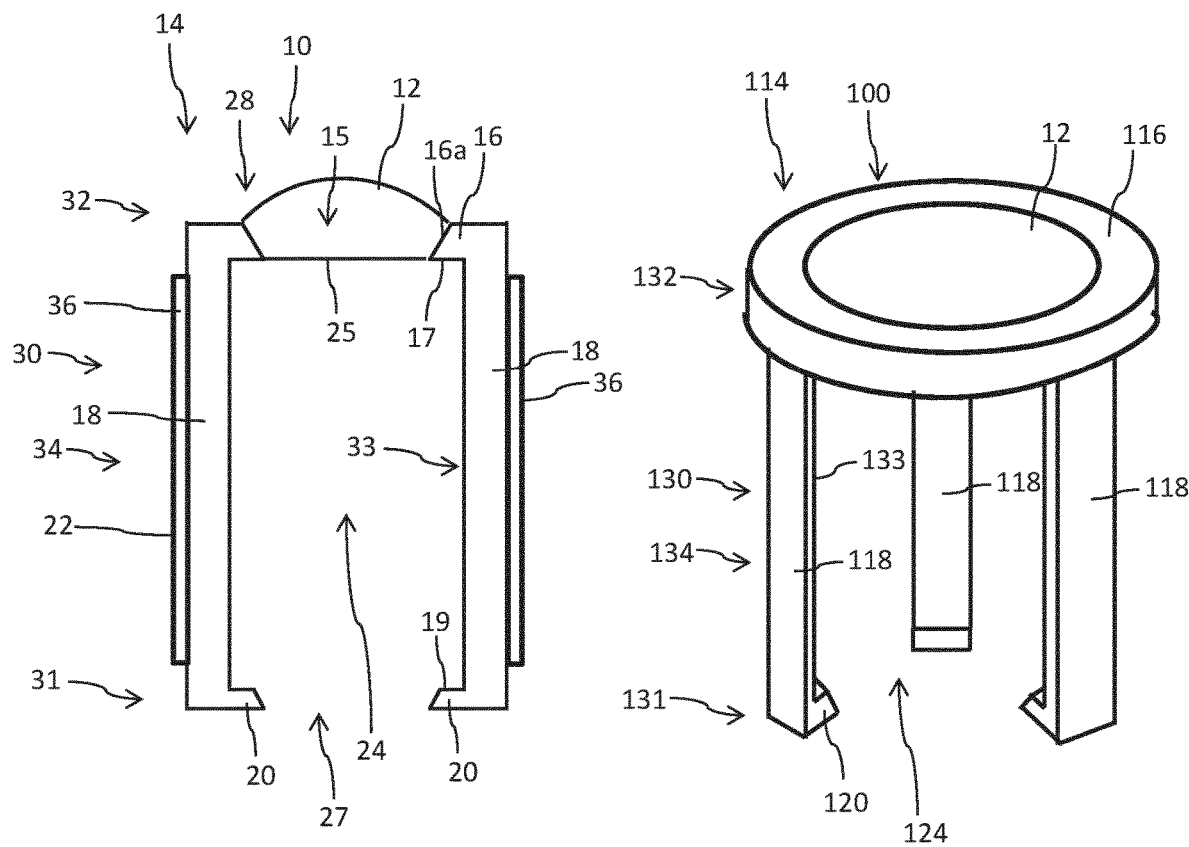
FIG. 2 shows the magnifying device according to FIG. 1 in a longitudinal cross-section.
FIG. 3 shows an alternative embodiment of the magnifying device, FIG. 4 schematically shows a perspective view of an injection device.

In FIGS. 1 and 2 a first embodiment of a magnifying device 10 is illustrated. As shown in FIGS. 1 and 2 the magnifying device 10 comprises a frame 14 having a proximal end 32 and an opposite distal end 31. The frame 14 further comprises a sidewall structure 30 extending from the proximal end 32 towards the distal end 31. In other words, the sidewall structure 30, hence the distal end thereof forms the distal end 31 of the frame 14. The sidewall structure 30 further defines a receptacle 24 having an insert opening 27 at the distal end 31. Near or at the proximal end 32 there is located a magnifying lens 12. The magnifying lens 12 extends at least partially across the proximal end 32 of the frame 14. The optical axis of the magnifying lens, extending vertical in the illustration according to FIG. 2 extends substantially parallel to an inside-facing portion 33 of the sidewall structure 30. When mounted and attached to the injection device, in particular to the proximal end 3a and hence to the dose selector 8 the optical axis of the magnifying lens 12 may coincide or at least extend parallel to the longitudinal direction of the injection device 9 as it is indicated by the distal direction 1 and the proximal direction 2 as shown in FIG. 4.

As it is further apparent from FIG. 2 the frame 14 features a through opening 15 in a radial central portion at its proximal end 32. The through opening 15 radially confined by a radially inwardly extending rim portion 16 of the frame 14 is covered by the magnifying lens 12. Moreover, the magnifying lens 12 is fitted into the rim portion 16 and is axially and radially confined by an abutment portion 16a at a radially inwardly-facing end section of the rim portion 16.

As can be further seen in FIG. 2 the magnifying lens 12 also confines and delimits the receptacle 24 in proximal direction 2. The proximal end face 25 of the lens 12 or the bottom of the receptacle 24 flushes with a distally-facing abutment portion 17 of the radially inwardly extending rim portion 16 of the frame 14. It is also conceivable, that the distally-facing surface of the magnifying lens 12 is located at an axial distance from the abutment portion 17. In particular, the overall shape, the curvature, the material as well as the axial position of the magnifying lens 12 relative to the frame 14 depends on the desired degree of magnification. The lens 12 may axially protrude from a proximal end face 28 of the frame 14. It is also conceivable that the magnifying lens 12 is located in an axial recess at the proximal end face 28 of the frame 14. the frame may provide a shock absorber for the magnifying lens as well as for the display arrangement 50 of the injection device 9.

Near the distal end 31 the sidewall structure 30 comprises at least one radially inwardly extending ledge 20 by means of which the frame 14 and hence the magnifying device 10 is attachable to the dose selector 8 of the injection device 9. The distal end 31 may exhibit a certain flexibility or elasticity by way of which the ledge 20 is pivotable or bendable radially outwardly as the frame 14 is pushed in axial direction onto the dose selector 8. When reaching a final assembly configuration as indicated in FIG. 7 the radially inwardly extending ledge 20 engages with a correspondingly-shaped radially inwardly extending ledge 8a or edge of the dose selector 8. Simultaneously, the distally-facing abutment face 17 on the rim portion 16 of the frame 14 axially abuts with the proximal end face 60 of the dose selector 8 as shown in FIG. 7. In order to provide a slack-free and slip-free attachment of the magnifying device 10 to the dose selector 8 the axial distance between the abutment face 17 and a proximally-facing abutment face 19 on the radially inwardly extending ledge 20 is directly correlated and matches with the axial extension of the dose selector 8.

It is further conceivable, that the sidewall structure 30, at least the ledge 20 exhibits a particular degree of elasticity in order to provide a slack-free attachment to the dose selector 8.

In the cross-section as illustrated in FIG. 7 the sidewall structure 30 comprises a conical profile extending radially outwardly towards the proximal end 32. In this way, the outer circumference as well as the radial diameter of the magnifying device 10 constantly increases towards the proximal end 32. This not only enables to make use of magnifying lenses 12 of larger diameter but also and predominantly serves to increase the outer surface or the outside-facing portion 34 of the sidewall structure 30. An increase of the diameter or the circumference of the magnifying device 10, its frame 14 and of its sidewall structure 30 inherently provides an increased outer gripping portion 22 or gripping surface, by way of which the overall handling and operation of the dose selector 8 is facilitated.

Figure 11:
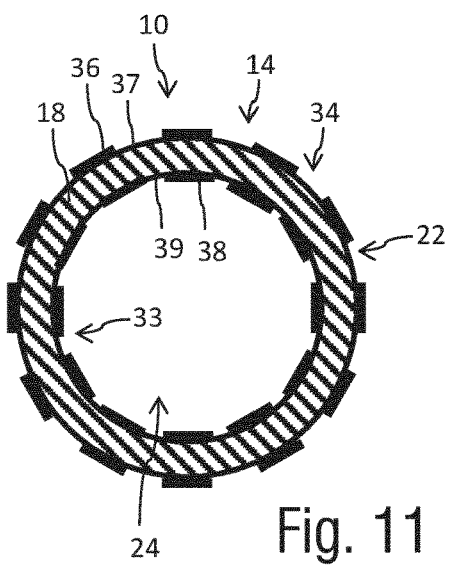
FIG. 11 shows a further embodiment of the magnifying device in cross-section.

In addition and as illustrated in FIGS. 2 and 11 the outside-facing portion 34, hence the radial outer surface of the sidewall structure 30 is provided with longitudinally, hence axially extending gripping ribs 36 that are arranged regularly spaced in circumferential direction along the outer circumference of the sidewall structure 30. Circumferentially between neighboring gripping ribs 36 there are provided gripping grooves 37. The alternating arrangement of gripping ribs 36 and gripping grooves 37 enhances a slip-free handling and hence a slip-free dialing of the dose selector 8 when the magnifying device 10 is attached. The gripping ribs 36 typically comprise an elastomeric material by way of which a friction between a user's hand or fingers and the magnifying device 10 can be increased. It is even conceivable that the entire sidewall structure 30 consists of an elastomeric material.

Apart from that also an inside-facing portion 33 of the e.g. tubular-shaped sidewall structure 30 may be provided with longitudinally or axially extending gripping ribs 38 radially inwardly protruding from the inside-facing portion 33 of the sidewall structure 30. Also the gripping ribs 38 may comprise an elastomeric material to increase the friction between the sidewall structure 30 and an outside-facing sidewall of the dose selector 8. In this way, the magnifying device 10 and its frame 14 is attachable to the dose selector 8 in a torque-proof manner. Alternatively or additionally, the radially inwardly extending gripping ribs 38 may be formed of a rather stiff or hard and inelastic material. Supposed that the dose selector 8 comprises a comparable or corresponding structure of gripping ribs 8b and gripping grooves 8c also a positive engagement of the sidewall structure 30 with the dose selector 8 is attainable.

In the alternative embodiment according to FIG. 3 the magnifying device 100 comprises a frame 114 having a magnifying lens 12 arranged in a rim portion 116 at a proximal end 132. There and in contrast to the magnifying device 10 according to FIG. 2 the sidewall structure 130 differs from a tubular or conical shape in that the sidewall structure 130 comprises numerous axially or longitudinally extending legs 118 extending from the proximal end 132 of the frame 114 towards its distal end 131. There and as illustrated in FIG. 3 the free and distal ends of the legs 118 comprise radially inwardly extending ledges 120 to engage with a correspondingly-shaped ledge 8a of the dose selector 8. The legs 118, hence the sidewall structure 130 formed by the legs 118 may also comprise gripping ribs 38 at an inside-facing portion 133. Alternatively or additionally also an outside-facing portion 134 of the sidewall structure 130 may be equipped with radially outwardly and longitudinally extending gripping ribs 36. The free ends of the legs 118 form the distal end 131 of the sidewall structure 130. Likewise the embodiment according to FIGS. 1 and 2 also the embodiment according to FIG. 3 comprises a receptacle 124 to receive the dose selector 8.

The free ends, hence the distal ends of the legs 118 are flexible in radial direction. They may be clipped or clamped over the dose selector 8 of the injection device 9. It is conceivable that the radial diameter of the receptacle 124 is slightly smaller than the diameter of cross-section of the dose selector 8. Hence, the legs 118 may be pre-tensed or biased radially inwardly so that they constantly exert a radially inwardly directed holding force to the dose selector 8 when assembled thereto.

The flexible legs 118 may further support an easy assembly and disassembly from the injection device. When attached to the injection device at least two of the flexible legs may be depressed radially inwardly, e.g. in a middle section with respect to their longitudinal direction, for instance with the help of the thumb and index finger of a user. In this way the legs may bend to form a concave shape as seen in longitudinal direction. As a consequence their distal end 131 and hence the ledges 120 then become subject to a radially outwardly directed displacement, thereby disengaging from an outer circumference of the dose selector 8 or of the injection device 9. Hence, by way of an elastic deformation of the legs 118, the disassembly and replacement of the magnifying device from the injection device is facilitated.

Figure 9:
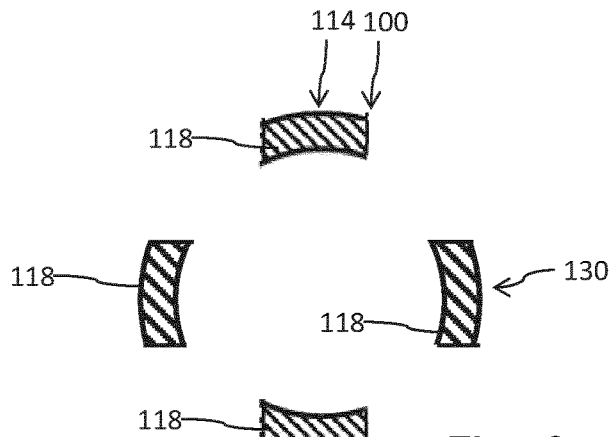

In the cross-section according to FIG. 9 an embodiment of a sidewall structure 130 of a magnifying device 100 is shown, wherein the legs 118 are somewhat arc-shaped in tangential or circumferential direction according to the outer circumference of the dose selector 8. In this way and with arc-shaped legs 118 or correspondingly arc-shaped ledges 120 a rather good and reliable mechanical fixing of the magnifying device 100 to the dose selector 8 can be obtained.

For the various embodiments as shown in FIGS. 1-3 and 7-11 it is of particular benefit when the radially inwardly extending rim portion 16 at the proximal end 32 of the frame comprises a proximally directed and radially inwardly extending abutment face 16a that is in axial abutment with the magnifying lens 12. As shown in FIG. 7, the abutment face 16a comprises a surface normal substantially extending in proximal direction 2. Moreover, the distally-facing abutment face 17 of the rim portion 16 is in direct abutment with the proximal end face 60 of the dose selector 8. The abutment face 16a is in direct abutment with a correspondingly-shaped and distally-facing circumferential abutment face of the magnifying lens 12.

In the assembly configuration as shown in FIG. 7 the rim portion 16 is axially sandwiched between the magnifying lens 12 and the proximal end face 60 of the dose selector 8. In this way, any distally directed pressure acting on the magnifying lens 12 is unalteredly transferable to the proximal end face 60 of the dose selector 8. Such an arrangement is of particular benefit when the dose selector 8 is axially distally depressible for inducing a dose dispensing or dose delivery procedure of the injection device 9.

Figure 8:
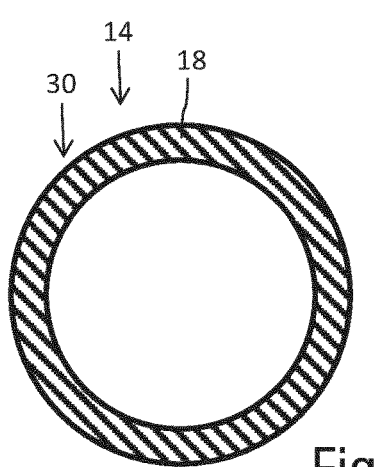
FIG. 8 is a schematic cross-section through the sidewall structure of the magnifying device according to one embodiment and FIG. 9 is a cross-section through the sidewall structure according to another embodiment, FIG. 10 schematically shows an alternative embodiment of the magnifying device in a longitudinal cross-section

In the further embodiment as shown in cross-section according to FIG. 8 the sidewall structure 30 of the frame 14 of the magnifying device is circular symmetric and comprises a rather plane and even-shaped inside-facing and outside-facing portion of its sidewall 18. In this embodiment the sidewall 18 is typically made of an elastomeric material, wherein the inner diameter of the sidewall 18 is slightly smaller than the outer diameter of the dose selector 8. In this way, the magnifying device 10 with its sidewall structure 30 is to be urged onto the dose selector in distal direction to form a force fit or a frictional engagement.

Figure 10:
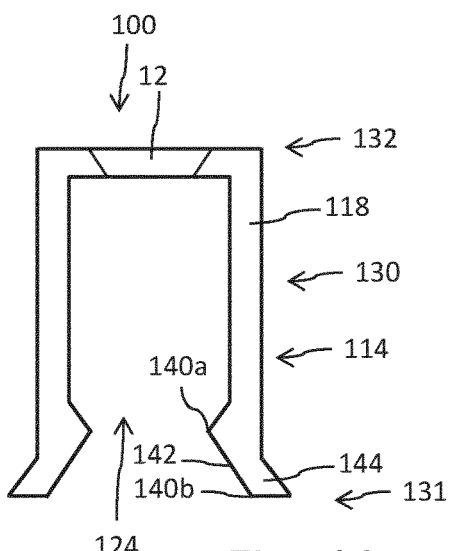

In the further embodiment according to FIG. 10 the sidewall structure 130 comprises at least two or even more parallel and substantially axially extending legs 118. Towards the distal end 131 the legs 118 protrude radially outwardly with a free end 144. Radially inwardly the free ends 144 each comprise a beveled edge 142 extending in proximal direction 2 radially inwardly. The beveled edge 142 forms a radially inwardly extending ledge 140. A proximal end 140a of the ledge 140 protrudes radially inwardly from an inside-facing surface portion of the respective leg 118. A distal end 140b of the ledge 140 forms and coincides with a distal end of the beveled edge 142. The geometrically and radially oppositely located ledges 140 of oppositely located legs 118 form a neck portion to positively engage with the ledge 8a of the dose selector 8.

In the embodiment according to FIG. 10 the distal end 140b of the ledge 140 is located radially outwardly from the body 3 and is also located at a certain radial distance from the body 3 so that a user may enter this radial gap between the distal end 140b and the body 3. In this way, the radially outwardly extending free end 144 of the ledge 140 serves as a gripping means to release and to disassemble the magnifying device 100 from the dose selector 8.

It is generally conceivable, that also the embodiments as shown in FIGS. 2, 3, 7, 8, 9 and 11 are provided with such a radially outwardly extending skirt portion of the distal end 140b of the sidewall structure 130.

LIST OF REFERENCE NUMBERS 1 distal direction
2 proximal direction
3 body
3a proximal end
4 drive mechanism
5 cartridge holder
6 socket
7 window
8 dose selector
8a ledge
8b rib
8c groove
9 injection device
10 magnifying device
12 magnifying lens
14 frame
15 through opening
16 rim portion
16a abutment portion
17 abutment face
18 sidewall
19 abutment face
20 ledge
22 gripping surface 24 receptacle
25 end face
27 insert opening
28 end face
30 sidewall structure
31 distal end
32 proximal end
33 inside-facing portion
34 outside-facing portion
36 gripping rib
37 gripping groove
38 gripping rib
39 gripping groove
50 display arrangement
51 number
52 cover
53 symbol
54 frame
56 dosing detector
58 display
60 proximal end face
70 cartridge
71 barrel
72 seal
73 piston
80 piston rod
82 pressure piece
100 magnifying device
114 frame
116 rim portion
118 leg
120 ledge
124 insert opening
130 sidewall structure
131 distal end
132 proximal end
133 inside-facing portion
134 outside-facing portion
140 ledge
140a proximal end
140b distal end
142 beveled edge
144 free end

The invention claimed is:

1. A magnifying device comprising:
a frame comprising a distal end, a proximal end opposite to the distal end, and a receptacle extending from the distal end towards the proximal end, wherein the receptacle is accessible from the distal end to receive a proximal end portion of an injection device therein; and
a magnifying lens fixed to the proximal end of the frame and extending at least partially across the proximal end of the frame,
wherein at least a portion of the magnifying device is attachable to the injection device;
wherein the frame comprises a sidewall structure to enclose a dose selector located at the proximal end portion of the injection device,
wherein the sidewall structure extends distally from the proximal end of the frame, and
wherein the sidewall structure is engageable with the dose selector in a torque proof manner.

2. The magnifying device according to claim 1, wherein the magnifying lens is arranged in a proximal end face of the frame.

3. The magnifying device according to claim 1, wherein the sidewall structure comprises a radially inwardly extending ledge at the distal end of the frame to axially engage with a radially inwardly extending ledge at a distal end of the dose selector.

4. The magnifying device according to claim 1, wherein the frame comprises a radially inwardly extending rim portion at the proximal end of the frame with a distally facing abutment face to axially abut with a proximal end face of the dose selector.

5. The magnifying device according to claim 4, wherein the rim portion comprises a proximally directed and radially inwardly extending abutment face axially abutting the magnifying lens.

6. The magnifying device according to claim 1, wherein the sidewall structure comprises a cylindrically or conically shaped sidewall.

7. The magnifying device according to claim 1, wherein the sidewall structure comprises a plurality of bendable legs extending distally and separated along a circumference of the proximal end of the frame.

8. The magnifying device according to claim 1, wherein the sidewall structure comprises axially extending gripping ribs on at least one of a radially outwardly facing portion of the sidewall structure or a radially inwardly facing portion of the sidewall structure.

9. The magnifying device according to claim 1, wherein at least a portion of the frame or a sidewall structure of the frame comprises an elastomeric material.

10. An injection device for administering a dose of a liquid medicament and comprising:
a housing to receive a cartridge having a barrel containing the medicament and having a piston axially displaceable inside the barrel;
a drive mechanism having a piston rod to operably engage with the piston;
a dose selector at a proximal end portion of the housing and being operable for setting the dose;
a display arrangement in a proximal end face of the dose selector to visualize a dose information; and
a magnifying device comprising
a frame comprising a distal end, a proximal end opposite to the distal end, and a receptacle extending from the distal end towards the proximal end, wherein the receptacle is accessible from the distal end to receive the proximal end portion of the injection device therein; and
a magnifying lens fixed to the proximal end of the frame and extending at least partially across the proximal end of the frame,
wherein at least a portion of the magnifying device is attachable to the injection device:
wherein the frame comprises a sidewall structure to enclose a dose selector located at the proximal end portion of the injection device,
wherein the sidewall structure extends distally from the proximal end of the frame, and
wherein the sidewall structure is engageable with the dose selector in a torque proof manner.

11. The injection device according to claim 10, wherein:
the dose selector is rotatable relative to the housing for setting of the dose, and
the magnifying device is in torque proof engagement with the dose selector.

12. The injection device according to claim 10, wherein the display arrangement comprises an electronic display arrangement to visualize a size of a last dose injected.

13. The injection device according to claim 12, wherein the electronic display arrangement is configured to visualize a time interval since the last dose was injected.

14. The injection device according to claim 10, further comprising a cartridge arranged inside the housing.

15. The injection device according to claim 10, wherein the magnifying lens covers at least a portion of the display arrangement.

16. The injection device according to claim 10, wherein the magnifying device is releasably attached to the proximal end portion of the injection device.

17. A method comprising:
attaching a magnifying device to a dose selector of an injection device such that a receptacle of a frame of the magnifying device receives a proximal end portion of the injection device and such that a magnifying lens of the magnifying device covers at least a portion of a display arrangement of the injection device, wherein:
the frame of the magnifying device comprises a distal end, a proximal end opposite to the distal end, and a receptacle extending from the distal end towards the proximal end; and
the magnifying lens of the magnifying device is fixed to the proximal end of the frame and extending at least partially across the proximal end of the frame,
wherein the frame comprises a sidewall structure to enclose a dose selector located at the proximal end portion of the injection device,
wherein the sidewall structure extends distally from the proximal end of the frame, and
wherein the sidewall structure is engageable with the dose selector in a torque proof manner; and
dispensing a dose of medicament from the injection device, thereby causing the display arrangement to visualize information related to the dose of medicament.

18. The method according to claim 17, wherein dispensing the dose of medicament further comprises causing the display arrangement to visualize a time interval since the dose was injected.

19. A magnifying device attachable to an injection device, the magnifying device comprising:
a frame comprising a distal end, a proximal end opposite to the distal end, and a receptacle extending from the distal end towards the proximal end, wherein the receptacle is accessible from the distal end to receive a proximal end portion of the injection device therein; and
a magnifying lens fixed to the proximal end of the frame and extending at least partially across the proximal end of the frame,
wherein the frame comprises a sidewall structure to enclose a dose selector at the proximal end portion of the injection device,
wherein the sidewall structure extends distally from the proximal end of the frame, and
wherein the sidewall structure comprises a plurality of bendable legs extending distally and separated along a circumference of the proximal end of the frame.

20. The magnifying device according to claim 1, wherein the dose selector of the injection device is rotatable relative to a body of the injection device for setting of a dose, and
wherein when the sidewall structure is in a torque-proof engagement with the dose selector the magnifying device is configured to induce a dose setting torque to the dose selector via the sidewall structure.

21. The magnifying device according to claim 1, wherein the sidewall structure is engageable with the dose selector in a torque proof manner with regard to a first sense of rotation and with regard to a second sense of rotation opposite to the first sense of rotation.

* * * * *

UNITED STATES PATENT AND TRADEMARK OFFICE
CERTIFICATE OF CORRECTION

PATENT NO. : 10,625,024 B2  
APPLICATION NO. : 15/549064  
DATED : April 21, 2020  
INVENTOR(S) : Zdenek Cerman Page 1 of 1

It is certified that error appears in the above-identified patent and that said Letters Patent is hereby corrected as shown below:

In the Claims

In Column 20, Line 52, Claim 10, delete "device:" and insert -- device; --

Signed and Sealed this
Twenty-ninth Day of September, 2020

Andrei Iancu
*Director of the United States Patent and Trademark Office*